United States Patent [19]

Yamamoto et al.

[11] Patent Number: 4,915,694
[45] Date of Patent: Apr. 10, 1990

[54] ANTIMICROBIAL WOUND DRESSING AND SKIN FIXATOR FOR PERCUTANEOUS CONDUITS

[75] Inventors: Ronald Yamamoto; Stanley R. Conston, both of Redwood City; Sophia Pesotchinsky, Palo Alto, all of Calif.

[73] Assignee: Vitaphore Corporation, Menlo Park, Calif.

[21] Appl. No.: 104,460

[22] Filed: Oct. 2, 1987

[51] Int. Cl.$^4$ .............................................. A61F 13/02
[52] U.S. Cl. .................................... 604/180; 604/307; 604/4
[58] Field of Search ............... 604/170, 179, 180, 304, 604/305, 307, 308

[56]           References Cited
          U.S. PATENT DOCUMENTS

| | | | |
|---|---|---|---|
| 3,683,911 | 8/1972 | McCormick | 604/180 |
| 3,939,831 | 2/1976 | Cioca et al. | 604/304 |
| 4,040,427 | 8/1977 | Winnie | 604/180 |
| 4,297,995 | 11/1981 | Golub | 604/308 |
| 4,340,043 | 7/1982 | Seymour | 604/307 |
| 4,579,120 | 4/1986 | MacGregor | 604/180 |
| 4,633,863 | 1/1987 | Filips et al. | 604/180 |
| 4,645,492 | 2/1987 | Weeks | 604/180 |

*Primary Examiner*—Dalton L. Truluck
*Assistant Examiner*—Denise W. DeFranco
*Attorney, Agent, or Firm*—Flehr, Hohbach, Test, Albritton & Herbert

[57]           ABSTRACT

An antimicrobial catheter shield is provided comprising an elastomeric catheter collar and a planar porous elastomeric peripheral flange, with an absorbent patch containing an antimicrobial agent attached to the surface of the flange opposite to the collar. A radial slit extends through the collar, flange and patch and the collar is adapted with a means for securing a catheter to prevent longitudinal motion of the catheter through the collar. The catheter shield provides an antimicrobial patch, as well as a longitudinal and lateral anchor for the catheter, which is easily applied and readily replaced.

4 Claims, 1 Drawing Sheet

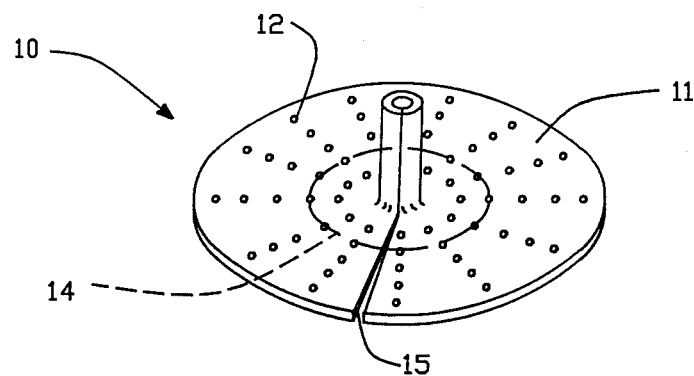
FIG.-1
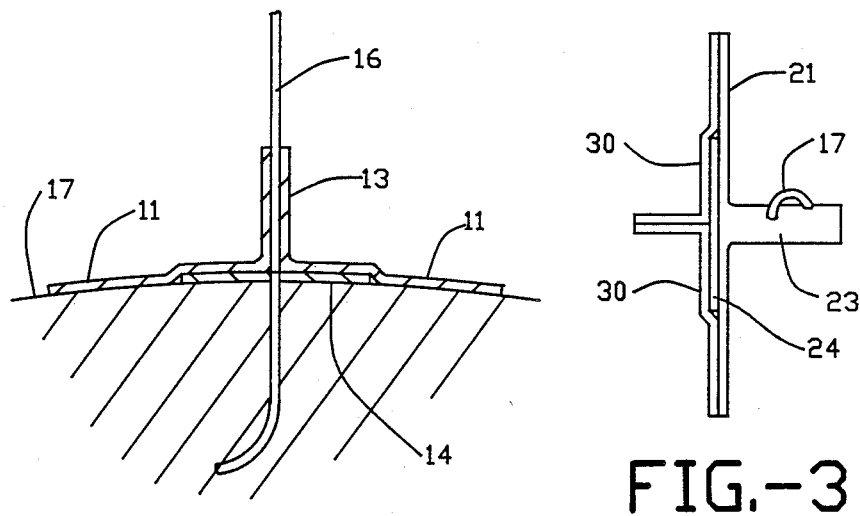
FIG.-2
FIG.-3
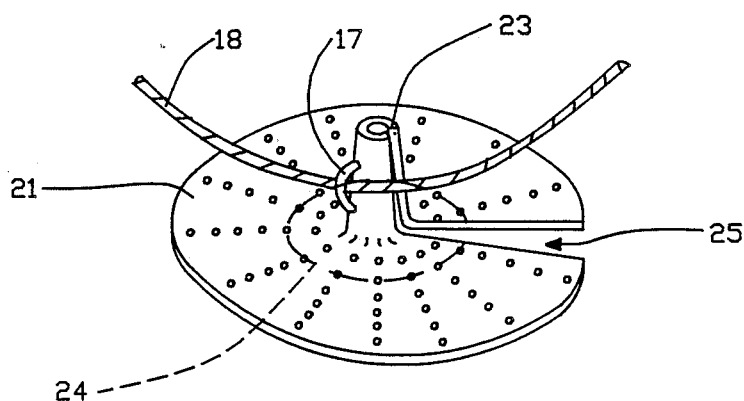
FIG.-4

4,915,694

ANTIMICROBIAL WOUND DRESSING AND SKIN FIXATOR FOR PERCUTANEOUS CONDUITS

The present invention is directed to a device which serves as an antimicrobial wound dressing, skin fixator and anchoring device for catheters.

BACKGROUND OF THE INVENTION

The use of percutaneous medical devices, such as catheters, which are normally used in medical practice to infuse or withdraw fluids and to monitor metabolic functions, cause a semi-permanent breach in the skin. This wound provides a path for normal skin microorganisms to invade along the catheter wound tract into deeper tissues, thus threatening the therapy being utilized and the health of the patient. Moreover, the potential for antimicrobial infection along the catheter tract is increased by movement of the catheter and by bacterial proliferation beneath the wound dressing which is usually used at the catheter exit site. Moreover tissues contacting the catheter are in a state of chronic inflammation, thus impairing the normal defense mechanisms against bacterial infection.

Thus it is an object of the present invention to stabilize a catheter at the wound site.

It is a further object of the present invention to provide an antimicrobial wound dressing at the exit site which can protect the wound site from the environment.

It is a further object of the invention to provide a device which can be used both to anchor a catheter and serve as a wound dressing, but which is disposable and readily replaced as needed without removing the catheter or without undue disruption at the wound site.

These and other objects will be apparent from the following description and from the practice of the invention.

SUMMARY OF THE INVENTION

The present invention is directed to an antimicrobial catheter shield comprising a central elastomeric catheter collar orthogonally disposed at one end thereof to a planar, porous peripheral elastomeric flange, the flange extending around the end of the collar; an absorbent patch containing an antimicrobial agent, the patch attached to the surface of the flange opposite to the collar at a central location of the flange, the patch having maximum dimensions less than the maximum dimensions of the flange; wherein the collar, flange and patch are characterized by a radial slit extending from the collar to the outer edge of the flange to provide a lateral insertion route for insertion of a catheter into the collar; the collar further being adapted with means for securing the collar around the catheter to prevent longitudinal motion of the catheter through the collar. The surface of the flange opposite to the collar bears an adhesive pressure-sensitive coating for adhering the shield to skin to prevent lateral motion of the shield and catheter and to hold the patch in contact with the wound site formed by the catheter.

BRIEF DESCRIPTION OF THE FIGURES

FIG. 1 is a perspective view of one embodiment of the present invention;

FIG. 2 is a schematic view showing the embodiment of FIG. 1 in use, with portions of the view in cross section;

FIG. 3 is a partial cross sectional view of a second embodiment of the invention;

FIG. 4 is a perspective view of the embodiment of FIG. 3 showing an exaggerated distention of the radial slit.

DESCRIPTION OF THE PREFERRED EMBODIMENTS

Referring to FIGS. 1 and 2, a catheter shield 10 formed of an elastomeric material such as polyurethane, by conventional vacuum formation, injection molding or other means, and is sterilizable and compatible with medication and body tissues. The shield 10 comprises a porous peripheral flange 11 which is made porous by ventilation holes 12 and/or micropores (not shown) of sufficient size to allow the passage of moisture therethrough. Co-formed with the flange 11 is central catheter collar 13 orthogonally projecting above the plane of the flange 11. Collar 13 may also be made separately and attached to flange 11 by, for example, gluing. On the underside of flange 11 as shown is an absorbent patch 14 containing an antimicrobial agent. The patch 14 is made of an absorbent material and is affixed to the bottom of the flange 11, for example, using a pressure-sensitive adhesive. In addition, the underside of the flange 11 (the side opposite to the collar 13) has over its entire surface a pressure-sensitive adhesive for attachment of the flange 11 to the skin of the patient, both to prevent lateral movement of the patch 14 and catheter (not shown) retained thereby, and to hold the patch 14 in close contact with the wound site formed by the catheter. As shown in FIG. 1, a radial slit 15 communicating the interior of collar 13 with the outer edge of flange 11 allows the insertion of a catheter into the collar 13 from a lateral direction.

In the embodiment shown in FIG. 1, the interior diameter of the collar 13 is such that it is approximately equal to the outer diameter of the catheter (not shown) to be inserted therein, therefore the frictional forces between the inner surface of the collar 13 and the outer surface of the catheter will be such that the catheter will be held tightly enough to avoid longitudinal movement of the catheter through the collar during normal use. The frictional contact of the collar 13 with the catheter may be further increased by a slight overlap of the edges of radial slit 15 when securing the catheter.

Referring to FIG. 2 the embodiment of FIG. 1 is shown with a catheter 16 penetrating through the skin 17 of a patient. The adhesive undersurface of flange 11 containing the pressure-sensitive adhesive is firmly attached to the skin 17, thereby holding the absorbent patch 14 in close contact in the vicinity of the wound caused by the catheter 16 penetrating the skin. The longitudinal movement of the catheter is prevented by the frictional forces between the outer surface of the catheter in contact with the inner surfaces of the collar 13.

Referring to FIG. 3 there is shown a partial cross sectional view of another embodiment of the present invention in which an eyelet 17 is co-molded or co-formed onto the exterior surface of the collar 23. The flange 21 and absorbent patch 24 are as described in connection with FIGS. 1 and 2. The additional features shown in FIG. 3 are the removable tabs 30 used to store the shield prior to use. The tabs 30 cover the lower adhesive surface of flange 21 and the exposed surface of patch 24 and may be made of any convenient material such as paper, or plastic. The tabs 30 are removed prior to use of the shield.

Referring to FIG. 4 there is shown a perspective view of the embodiment of FIG. 3 with an exaggerated distention of the radial slit 25 (not shown in FIG. 3). In FIG. 4, the tabs 30 of FIG. 3 have been removed and a suture thread 18 has been inserted into the eyelet 17. After placement of the catheter (not shown) through the radial slit 25 into the collar 23 the catheter is secured by wrapping the suture thread 18 around the collar 23 and securing by tying a knot.

The antimicrobial material contained in the patch 14, 24, may be any available antimicrobial agent such as chlorhexidene or antimicrobial silver salt. In one particularly preferred embodiment the patch 14, 24 will be made of collagen and the antimicrobial agent will be absorbed therein. The collagen will serve as a antimicrobial drug reservoir whereby the antimicrobial drug will be released gradually, thus providing a long-acting antimicrobial surface at the wound site.

In one modification, the flange 11, 21 and/or collar 13, 23 may be impregnated with the antimicrobial agent to further reduce the risks of infection at the wound site. This is advantageous because incidental axial movement of the catheter through the collar 13, 23 would result in a squeegee effect whereby bacteria are wiped off the catheter surface as it passes through the collar and into tissues, and antimicrobial agent is wiped over the catheter to further deter infection.

The catheter shield according to the present invention may be used with any type of percutaneous device, particularly with epidural catheters, arterial catheters, central venous catheters, umbilical catheters, wound drains, and bone fixation pins.

Having described the preferred embodiments of the present invention, it will be apparent to those skilled in the art that various modifications and variations may be made within the spirit and scope of the invention. The present invention is not to be limited except by the scope of following claims.

What is claimed is:

1. An antimicrobial catheter shield comprising a central elastomeric collar having a longitudinal orifice and having one end of said collar orthogonally disposed to a planar, elastomeric, porous, peripheral flange, said flange extending around said end of said collar, an absorbent patch comprising collagen and containing an antimicrobial agent peripherally and centrally attached to the surface of said flange opposite to said collar, said collagen serving as an antimicrobial drug reservoir and said antimicrobial agent selected from the group consisting of chlorhexidene and silver salts, the maximum dimensions of said patch being less than the maximum dimensions of said flange;

wherein a radial slit extends through said collar, flange and patch from said longitudinal orifice of said collar to the outer edge of said flange to provide a lateral insertion route of a catheter into said collar;

said collar adapted with means for securing said collar around a catheter to prevent longitudinal motion of said catheter through said collar;

a pressure-sensitive adhesive coating on the lower surface of said flange; and one or more tabs removably adherent to said pressure-sensitive coating and at least coextensive with said flange and cofacial to said patch.

2. A catheter shield according to claim 1 wherein said means for securing said catheter comprises an eyelet on the exterior surface of said collar for accommodating tying means circumferentially tightenable around said collar.

3. A catheter shield according to claim 1 wherein said flange is microporous to enhance vapor transmission therethrough.

4. A catheter shield according to claim 1 wherein said antimicrobial agent comprises chlorhexidene.

* * * * *